(12) United States Patent
Machhammer et al.

(10) Patent No.: US 8,338,640 B2
(45) Date of Patent: Dec. 25, 2012

(54) HETEROGENEOUSLY CATALYZED PARTIAL DIRECT OXIDATION OF PROPANE AND/OR ISOBUTANE

(75) Inventors: Otto Machhammer, Mannheim (DE); Sven Crone, Limburgerhof (DE); Frieder Borgmeier, Mannheim (DE); Klaus Joachim Mueller-Engel, Stutensee (DE); Christoph Adami, Weinheim (DE); Armin Diefenbacher, Germersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 2602 days.

(21) Appl. No.: 10/815,873

(22) Filed: Apr. 2, 2004

(65) Prior Publication Data
US 2004/0204607 A1     Oct. 14, 2004

Related U.S. Application Data

(60) Provisional application No. 60/461,136, filed on Apr. 9, 2003.

(30) Foreign Application Priority Data

Apr. 9, 2003 (DE) .................................. 103 16 465

(51) Int. Cl.
C07C 51/16 (2006.01)
(52) U.S. Cl. .................................................... 562/549
(58) Field of Classification Search .................. 562/549
See application file for complete search history.

(56) References Cited

U.S. PATENT DOCUMENTS

| 3,766,286 | A | * | 10/1973 | Olah | 585/480 |
| 4,220,802 | A | * | 9/1980 | Akiyama et al. | 562/535 |
| 5,380,933 | A | * | 1/1995 | Ushikubo et al. | 562/549 |
| 6,596,901 | B1 | | 7/2003 | Eck et al. | |
| 6,679,939 | B1 | | 1/2004 | Thiel et al. | |
| 6,858,754 | B2 | * | 2/2005 | Borgmeier | 562/547 |

FOREIGN PATENT DOCUMENTS

| DE | 198 35 247 | 2/1999 |
| DE | 199 24 532 | 11/2000 |
| DE | 100 51 419 | 4/2002 |
| DE | 101 22 027 | 5/2002 |
| DE | 101 19 933 | 10/2002 |
| DE | 102 54 279 | 6/2004 |
| DE | 102 61 186 | 7/2004 |
| EP | 0 495 504 | 7/1992 |
| EP | 0 529 853 | 3/1993 |
| EP | 0 603 836 | 6/1994 |
| EP | 0 608 838 | 8/1994 |
| EP | 0 895 809 | 2/1999 |
| EP | 1 090 684 | 4/2001 |
| EP | 1 192 987 | 4/2002 |
| EP | 1 193 240 | 4/2002 |
| EP | 1 254 707 | 11/2002 |
| EP | 1 254 709 | 11/2002 |
| JP | 2000-095725 | 4/2000 |
| WO | 98/01415 | 1/1998 |
| WO | WO 99/20590 | 4/1999 |

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

A process for heterogeneously catalyzed partial direct oxidation of propane and/or isobutane, in which target product is removed in a workup stage from the product gas mixture obtained in the reaction stage, the remaining residual product gas mixture is divided into two portions of the same composition, one portion is recycled into the reaction stage and the other portion is discharged, and both the reaction stage and the workup stage are operated at elevated pressure.

32 Claims, 3 Drawing Sheets

HETEROGENEOUSLY CATALYZED PARTIAL DIRECT OXIDATION OF PROPANE AND/OR ISOBUTANE

CROSS-REFERENCE TO RELATED APPLICATIONS

Figure 1:
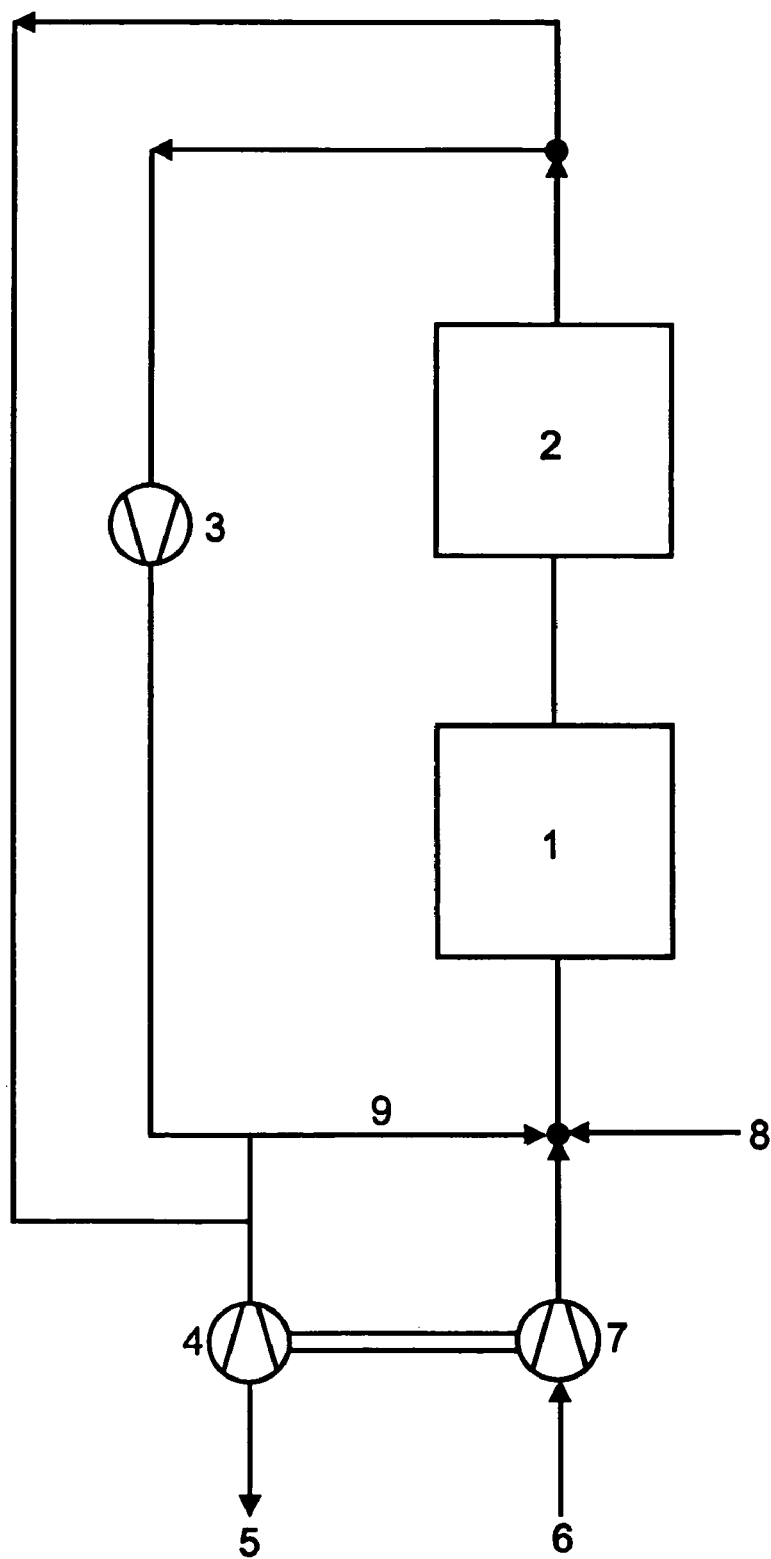

This application is a non-provisional application derived from provisional application Ser. No. 60/461,136 filed Apr. 9, 2003.

The present invention relates to a process for heterogeneously catalyzed partial direct oxidation of propane and/or isobutane to at least one of the target products acrylic acid, methacrylic acid, by feeding a starting reaction gas mixture comprising propane and/or isobutane, molecular oxygen and at least one inert diluent gas and having a inlet pressure $P^1$ to a reaction stage which, apart from an inlet for the starting reaction gas mixture, optionally further inlets for auxiliary gases, and an outlet for the product gas mixture, is sealed on the gas side, in the reaction stage directly oxidizing the propane and/or isobutane present in the starting reaction gas mixture partially to at least one target product by passing the starting reaction gas mixture at elevated temperature over a solid state catalyst, and conducting the reaction gas mixture as a product gas mixture comprising at least one target product and having the outlet pressure $P^2$ out of the reaction stage and, with this pressure $P^2$, into a workup stage which, apart from an inlet for the product gas mixture, optionally further inlets for auxiliary gases, and an outlet for the residual product gas mixture, is sealed on the gas side, in the workup stage basically separating target product present in the product gas mixture of the reaction stage from said product gas mixture into a liquid phase and conducting the remaining residual product gas mixture which comprises not only propane and/or isobutane and also in some cases propene and/or isobutene and has the outlet pressure $P^3$, where $P^3 < P^1$, out of the workup stage and recycling propane and/or isobutane present in the residual product gas mixture into the reaction stage.

Acrylic acid and methacrylic acid are important intermediates, for example for the preparation of polymers.

Their preparation by heterogeneously catalyzed partial direct oxidation of propane and/or isobutane in a reaction stage is known (cf., for example, EP-A 529853, EP-A 603836, EP-A 608838, EP-A 895809, DE-A 19835247, DE-A 10051419, DE-A 10122027, EP-A 1254707, EP-A 1254709, EP-A 1192987, EPA 1090684, DE-A 10254279 and literature cited in these documents).

The oxidizing agent used is normally molecular oxygen which can be added to the starting reaction gas mixture, for example, in pure form or in a mixture with gases which behave substantially inertly with respect to the partial oxidation (for example $N_2$ in air). Inert diluent gases, such as $N_2$, $H_2O$, $CO$, $CO_2$, He and/or Ar etc., absorb the heat of reaction and keep the reaction gas mixture outside the explosion range. In this document, inert diluent gases are generally those gases of which less than 5 mol %, preferably less than 3 mol % and more preferably less than 2 mol % are converted on single pass of the reaction gas mixture through the partial oxidation. The catalysts used are generally multielement oxides in the solid state. It is possible to carry out the reaction stage over multielement oxides in the solid state either in a fixed catalyst bed, fluidized catalyst bed or moving catalyst bed.

According to the teaching of the prior art, the working pressure in the reaction stage may be either below atmospheric pressure (=1 bar) or above 1 bar (cf., for example, DE-A 19835247, EP-A 895809 and DE-A 10261186). In general, it is slightly above atmospheric pressure for the purpose of overcoming the flow resistances in the reaction stage.

A disadvantage of the heterogeneously catalyzed partial direct oxidation of propane and/or isobutane to at least one of the target products acrylic acid, methacrylic acid is the comparatively pronounced unreactivity of propane and isobutane. This is the cause of only partial conversion of propane and/or isobutane generally being achieved on single pass of the reaction gas mixture through the appropriate reaction stage even at elevated temperatures.

One objective of the heterogeneously catalyzed partial direct oxidation of propane and/or isobutane to at least one of the target products acrylic acid, methacrylic acid is therefore to achieve a very high conversion of propane and/or isobutane coupled with simultaneously very high selectivity of target product formation at very low temperatures on single pass of the reaction gas mixture through the reaction stage, i.e. a very high space-time yield of target product coupled with very low energy demands.

A further requirement for economic performance of a heterogeneously catalyzed partial direct oxidation of propane and/or isobutane to at least one of the desired target products is the substantial recycling of unconverted propane and/or isobutane present in the product gas mixture into the reaction stage. To this end, the prior art makes the following suggestions.

In the preparation of acrylic acid by heterogeneously catalyzed partial direct oxidation of propane, DE-A 10119933 recommends the basic separation of acrylic acid present in the product gas mixture from said product gas mixture by absorption into a liquid absorbent, and the subsequent rectificative, extractive and/or crystallizative workup of the resulting liquid mixture of absorbent and acrylic acid in a manner known per se as far as glacial acrylic acid, or conducting the basic separation of acrylic acid from the product gas mixture into a liquid phase by fractional condensation, as described, for example, in DE-A 19924532 and further purifying the resulting aqueous acrylic acid condensate, for example by fractional crystallization.

With regard to the residual product gas mixture comprising unconverted propane in such basic separation of the acrylic acid into a liquid phase, DE-A 10119933 recommends removing the propane from the residual product gas mixture and recycling the propane which has been removed into the partial direct oxidation to acrylic acid. The removal methods recommended for this purpose are, for example, fractional pressure rectification or extraction with a hydrophobic organic solvent (which is capable of preferentially absorbing the propane) and subsequent desorption and/or stripping with air for the purpose of releasing the propane.

In complete agreement, EP-A 1193240, for the partial direct oxidation of alkanes such as propane, recommends removing (for example absorptively or adsorptively) the unconverted alkane present in the residual product gas mixture (as in the above prior art document, preferably together with alkene formed as a by-product) from said residual product gas mixture, and recycling it into the partial oxidation.

However, a disadvantage of the recycling of unconverted alkane and any alkene formed as a by-product into the reaction stage in accordance with the recommendations of the prior art is that the removal of the alkane and any alkene from the residual product gas mixture in which the unconverted alkane is normally present in a comparatively high dilution is comparatively costly and inconvenient and is associated with particularly high pressure drops. The latter discourages employment of elevated pressures in the reaction stage, since, in the recycling of the propane which has been removed, recompression always has to be effected to these pressures.

Another disadvantage is that other constituents which are present in the residual product gas mixture and have an advantageous effect on the heterogeneously catalyzed partial direct oxidation (for example steam, which generally supports activity and selectivity of the catalytically active composition, or residual oxygen, which does not have to be highly compressed) are not recycled into the reaction stage (but rather discharged) and, if required, always have to be added again fresh.

An additional cause of the suggestion of recycling unconverted hydrocarbon present in the residual product gas mixture separately into the reaction stage might, inter alia, be the consideration of keeping the amount of gas to be recycled (and thus also the amount of starting reaction gas mixture) very low, in order, in this way, to minimize the conveyor and compressor power to be employed in this connection (the recycled gas has to be recompressed to the inlet pressure of the reaction gas mixture before entry into the reaction stage, since, on the path through the reaction stage, the workup stage and the removal from the residual product gas mixture, it undergoes a pressure drop which is used to overcome the flow resistances and has to be restored) and also the required volumes. A further objective might also be to keep the feedstock losses at a minimum.

It is an object of the present invention to provide a process for heterogeneously catalyzed partial direct oxidation of propane and/or isobutane to at least one of the target products acrylic acid, methacrylic acid, in which the compressor power to be employed and the feedstock losses are minimized in another, more advantageous manner, and, at the same time, the space-time yield is optimized with minimized energy demands.

We have found that this object is achieved by a process for heterogeneously catalyzed partial direct oxidation of propane and/or isobutane to at least one of the targets products acrylic acid, methacrylic acid, by feeding a starting reaction gas mixture comprising propane and/or isobutane, molecular oxygen and at least one inert diluent gas and having a starting pressure $P^1$ to a reaction stage which, apart from an inlet for the starting reaction gas mixture, optionally further inlets for auxiliary gases, and an outlet for the product gas mixture, is sealed on the gas side, in the reaction stage directly oxidizing the propane and/or isobutane present in the starting reaction gas mixture partially to at least one target product by passing the starting reaction gas mixture at elevated temperature over a solid state catalyst, and conducting the reaction gas mixture as a product gas mixture comprising at least one target product and having the outlet pressure $P^2$ out of the reaction stage and, with this pressure $P^2$, into a workup stage which, apart from an inlet for the product gas mixture, optionally further inlets for auxiliary gases, and an outlet for the residual product gas mixture, is sealed on the gas side, in the workup stage basically separating target product present in the product gas mixture of the reaction stage from said product gas mixture into a liquid phase and conducting the remaining residual product gas mixture which comprises not only propane and/or isobutane and also in some cases propene and/or isobutene and has the outlet pressure $P^3$, where $P^3<P^1$, out of the workup stage and recycling propane and/or isobutane present in the residual product gas mixture into the reaction stage, which comprises selecting $P^1$ in such a way that $P^3 \geq 1.5$ bar and dividing the residual product gas mixture into two portions of the same composition and discharging one portion as output and recycling the other portion as cycle gas and feeding it back to the reaction stage, compressed to the inlet pressure $P^1$, as a constituent of the starting reaction gas mixture. Among other ways, the process according to the invention differs from the procedure disclosed in EP-A 495504 in that it has no catalytic carbon monoxide oxidation in and/or after the workup stage and before the output. Nor does the process according to the invention require any carbon dioxide scrubbing of the residual product gas mixture.

When propene and/or isobutene are by-produced in the reaction stage, these compounds normally remain combined with the propane and/or isobutane through the workup stage and are recycled together into the reaction stage in the cycle gas.

All pressure data in this document refer, unless explicitly stated otherwise, to absolute pressures.

Normally, the residual product gas mixture contains at least 2% by volume, or at least 5% by volume, usually at least 10% by volume, of constituents other than propane and/or isobutane and also than propene and/or isobutene and also, where present, than oxygen (for example CO, $CO_2$, $H_2O$ and/or $N_2$ etc.) (in general these are constituents present in the product gas mixture which have a lower boiling point than the target product (at atmospheric pressure)).

While the organic precursor compound (i.e. the propane and/or isobutane) which is to be partially oxidized in the process according to the invention is in practice frequently stored in liquid form, but is gaseous at standard temperature and pressure, simple evaporation generally suffices to bring the organic precursor compound to reaction stage inlet pressure. Steam which is optionally used as an inert diluent gas is available from a wide variety of sources, usually likewise with sufficient superatmospheric pressure.

However, this is generally not true at least for the oxygen source (for example air or oxygen-depleted air), any other inert diluent gases and in particular not for the propane-containing cycle gas (which normally has the reaction stage inlet pressure $P^1$ minus the pressure drop on the path through the reaction stage and through the workup stage and also the divider into the two portions; it is recycled into the reaction stage in the process according to the invention normally via pipes which are free of internals without significant additional pressure drop).

In practice, it is therefore normally necessary to bring at least a portion (at least the cycle gas) of the constituents of the starting reaction gas mixture from a lower starting pressure to a higher end pressure (the inlet pressure $P^1$ into the reaction stage) by means of a compressor.

These constituents (for example the oxygen source air and the cycle gas) can be compressed in spatially separated compressors or in a single compressor.

In principle, the compressors used for this compression of the gases mentioned may be of a wide variety of types. Cited by way of example are displacement compressors (for example piston compressors, screw compressors and rotary piston compressors), flow compressors (for example turbocompressors, centrifugal compressors, axial compressors and radial compressors) and jet compressors. According to the invention, preference is given to radial compressors, as described, for example, in DE-A 10259023.

According to the invention, preference is also given to proceeding in such a way that portions of the starting reaction gas mixture which stem from various sources and are substantially at reaction stage inlet pressure (or have been brought thereto), coming from separate lines, are initially usually mixed in a mixer, for example a static mixer (chambers having internals which have an increased mixing action compared to empty pipes), and subsequently, optionally heated to inlet temperature, fed to the reaction stage.

The entry of the individual gases into the line feeding the static mixer is appropriately selected in such a way that the formation of explosive mixtures is prevented (in the case of an inventive partial oxidation, this entry sequence is appropriately, for example, as follows: first cycle gas and/or steam, then air and finally the organic precursor compound). The steam content of the starting reaction gas mixture may of course also be added in such a way that finely divided liquid water droplets are metered into a starting reaction gas precursor mixture heated substantially to reaction temperature by indirect heat exchange with the product gas stream, and said water droplets evaporate spontaneously by absorbing heat to form the starting reaction gas mixture. Alternatively, the preheated starting reaction gas precursor mixture can be conducted via a gas saturator (gas mixture and water are conducted in co- or countercurrent over a large surface area).

The outlet pressure $P^3$ selected in accordance with the invention thus affects substantially the compressor power for the purpose of compressing the cycle gas and the oxygen source.

From an application point of view, the pressure $P^3$ with which the residual product gas mixture leaves the workup stage in the process according to the invention is generally not more than 30 or 25 bar, frequently not more than 20 bar. According to the invention, the outlet pressure $P^3$ is advantageously $\geq 1.5$ bar and $\leq 10$ bar, preferably $\geq 2$ bar and $\leq 8$ bar, frequently $\geq 3$ bar and $\leq 6$ bar or $\leq 5$ bar (for example 4 bar).

In other words, the characterizing feature of the process according to the invention is the operation of both the reaction stage and the workup stage at elevated pressure.

Such a procedure is advantageous for the following reasons:
- it has been found that, surprisingly, the heterogeneously catalyzed partial direct oxidation of propane and/or isobutane at elevated pressure leads to increased conversions under otherwise identical reaction conditions and based on single pass, without being accompanied by a significant reduction in the selectivity of target product formation;
- operation of the workup stage too at elevated pressure enables even increased amounts of cycle gas to be conveyed in comparatively small volumes required therefor and with comparatively low pressure drops incurred, since both the conveying volume of a given amount of gas and the pressure drop associated with conveying it generally decrease with increasing pressure; the latter reduces the compressor power required for the cycle gas compression to the inlet pressure $P^1$ of the reaction stage; at the same time, an increasing amount of cycle gas compared to the output amount minimizes the losses of unconverted propane and/or isobutane present in the output;
- the recycling of the propane without preceding removal thereof from the residual product gas mixture prevents the pressure drops which are necessarily associated with such a removal and ensures the simultaneous and energetically advantageous recycling of other constituents which are in some cases present in the residual product gas mixture, for example steam and $O_2$.

In other words, the comparatively simple measure of increasing the pressure allows, in accordance with the invention, all advantageous characteristics of the prior art process likewise to be achieved overall, without requiring a costly and inconvenient removal of the unconverted alkane and any alkene from the residual product gas mixture for this purpose (which additionally avoids undesired disadvantages, for example complete nonrecycling or energetically demanding recycling of steam), and at the same time, the measure of increasing the pressure results in an increase in the reactant conversion based on single throughput through the reaction stage without a significant decrease in the target product selectivity.

In this document, the term "reaction stage" or "workup stage" is in particular-one or more apparatus units connected in series which, apart from inlet and outlet and optionally any further inlets for auxiliary gases, are sealed on the gas side, so that the pressure drop to which a gas mixture is subject on passing through such an apparatus unit or through such a series connection of apparatus units is restricted to the overcoming of the flow resistances.

For example, the apparatus unit (or a series connection of such units) may be a tube bundle reactor, a fluidized bed reactor, a series connection of such reactors, an absorption column, a rectification column, a condensation column or a series connection of such columns or individual quench stages. A reactor as described above may of course also include the possibility of adding, for example, catalyst activator to the reactor while carrying out the process according to the invention, as described, for example, by WO 02/081421. In the process according to the invention, the term auxiliary gas is intended to include the possibility, in the case of a series connection of reactors, of supplementing inert gas and/or oxygen (for example air) between the reactors, or, in the workup stage, for example for polymerization inhibition reasons, of conducting a molecular oxygen-containing gas (for example air) together with the product gas mixture through the workup stage. Typically, the pressure drops in the process according to the invention over the reaction stage are from 0.1 to 3 bar, frequently from 0.3 to 1 or 0.5 bar, and, over the workup stage, from 0.5 to 3 bar, frequently from 1 to 2 bar.

When the process according to the invention is carried out in the region of particularly high pressures, the pressure drops, both in the reaction stage and in the workup stage, may be distinctly lower and attain, for example, 0.05 bar and smaller.

In the process according to the invention, the pressure $P^1$ at the inlet into the reaction stage, depending on the type of the workup stage employed, will be from 0.5 or 1 to 4 bar, usually from 1.5 to 3.5 bar, in many cases from 2 to 3 bar, above the pressure $P^3$ at the outlet of the workup stage.

When the process according to the invention is carried out in the region of particularly high pressures, the pressure $P^1$ at the inlet into the reaction stage is generally less than 0.5 bar (for example 0.1 or 0.01 bar) above the pressure $P^3$ at the outlet of the workup stage.

Typical pressures $P^1$ at the inlet into the reaction stage are therefore from 2.5 to 25 bar. In general, the pressure $P^1$ at the inlet into the reaction stage will be from 3 to 10 bar, and, appropriately in accordance with the invention, from 4 to 8 bar.

Typical pressures $P^2$ at the inlet into the workup stage are from 3 to 25 bar, frequently from 3 to 20 bar, or from 3 to 15 bar, or from 3 to 8 bar.

The control of the pressure ratios in the process according to the invention is possible in a simple manner, for example, by means of a throttle apparatus at the outlet for the portion of the residual product gas mixture to be discharged. In the process according to the invention, in addition to the advantages already described, an expander (inverse compressor through which the discharge is effected) connected in series instead of the throttle apparatus can also be used, when discharging one portion of the residual product gas mixture by its controlled decompression to atmospheric pressure to recover a portion of the compressor power required to compress the other portion of the residual product gas mixture and/or of the oxygen source (for example air) which has been circulated to the inlet pressure $P^1$.

The ratio of that portion of the residual product gas mixture which is recycled as cycle gas in the process according to the invention to that portion of the residual product gas mixture which is discharged as output depends in each case on the composition of the starting reaction gas mixture. However, R will generally be $\geq 0.5$ or $\geq 1$, usually $\geq 1.5$, preferably $\geq 2$, more preferably $\geq 3$. It will be appreciated that R in the process according to the invention may also be $\geq 8$ or $\geq 10$. Normally, R in the process according to the invention will be $\leq 30$, usually $\leq 25$, frequently $\leq 20$. Often, R will be $\leq 15$ or $\leq 10$, preferably from 2 to 8.

Otherwise, the process according to the invention can be carried out in a similar manner to the prior art processes for heterogeneously catalyzed partial oxidation of propane and/or isobutane to at least one of the target products.

In other words, the source of the molecular oxygen required for the purposes of the process according to the invention is either air or air depleted in molecular nitrogen (for example $\geq 90\%$ by volume of $O_2$, $\leq 10\%$ by volume of $N_2$), or else pure molecular oxygen or mixtures of molecular oxygen and other inert gases.

Useful catalysts for the process according to the invention are in principle all of those which are recommended in the prior art for the heterogeneously catalyzed partial direct oxidation of propane and/or isobutane to at least one of the target products.

These are, for example, catalysts of the documents JP-A 3-170445, EP-A 609122 and EP-A 747349.

It is essential to the invention that substantially all catalysts for each of the inventively possible heterogeneously catalyzed partial direct oxidations can be used.

The active compositions of these catalysts are generally multielement oxides, usually multimetal oxides.

The multimetal oxides which are suitable for the process according to the invention are in particular the multimetal oxides of the documents EP-A 608838, EP-A 529853, DE-A 10254279, DE-A 19835247, EP-A 895809, JP-A 7-232071, JP-A 11-169716, DE-A 10261186, EP-A 1192987, JP-A 10-57813, JP-A 2000-37623, JP-A 10-36311, WO 00/29105, EP-A 767164, DE-A 10029338, JP-A 8-57319, JP-A 10-28862, JP-A 11-43314, JP-A 11-574719, WO 00/29106, JP-A 10-330343, JP-A 11-285637, JP-A 310539, JP-A 11-42434, JP-A 11-343261, JP-A 3423262, WO 99/03825, JP-A 7-53448, JP-A 2000-51693, JP-A 11-263745, DE-A 10046672, DE-A 10118814, DE-A 10119933, JP-A 2000/143244, EP-A 318295, EP-A 603836, DE-A 19832033, DE-A 19836359, EP-A 962253, DE-A 10119933, DE-A 10051419, DE-A 10046672, DE-A 10033121, DE-A 10145958, DE-A 10122027, EP-A 1193240 and the literature cited in these documents.

The active composition of the catalyst charge to be used in the aforementioned cases is substantially multimetal oxide compositions which comprise the elements Mo, V, at least one of the two elements Te and Sb, and at least one of the elements from the group consisting of Nb, Ta, W, Ti, Al, Zr, Cr, Mn, Ga, Fe, Ru, Co, Cs, Ca, Sr, Ba, Rh, Ni, Pd, Pt, La, Pb, Cu, Re, Ir, Y, Pr, Nd, Tb, Bi, B, Ce, Sn, Zn, Si, Na, Li, K, Mg, Ag, Au and In in combination.

From the last element group, the combination preferably comprises the elements Nb, Ta, W and/or Ti and more preferably the element Nb.

The relevant multimetal oxide active compositions preferably comprise the aforementioned element combination in the stoichiometry I $$Mo_1V_bM^1_cM^2_d \tag{I}$$

where
$M^1$=Te and/or Sb,
$M^2$ at least one of the elements from the group consisting of Nb, Ta, W, Ti, Al, Zr, Cs, Ca, Sr, Ba, Cr, Mn, Ga, Fe, Ru, Co, Rh, Ni, Pd, Pt, La, Bi, Pb, Cu, Re, Ir, V, Pr, Nd, Tb, Ce, Sn, Zn, Si, Na, Li, K, Mg, Ag, Au and In,
b=from 0.01 to 1,
c=from >0 to 1, and
d=from >0 to 1.

According to the invention, preference is given to $M^1$=Te and $M^2$ Nb, Ta, W and/or Ti. Preference is given to $M^2$=Nb.

The stoichiometric coefficient b is advantageously from 0.1 to 0.6. Correspondingly, the preferred range for the stoichiometric coefficient c extends from 0.01 to 1 or from 0.05 to 0.4, and favorable values for d are from 0.001 to 1 or from 0.01 to 0.6.

According to the invention, it is particularly favorable when the stoichiometric coefficients b, c and d are simultaneously within the aforementioned preferred ranges.

The aforementioned is especially true when the active composition of the catalyst charge, with regard to its elements other than oxygen, consists of an aforementioned element combination.

These are then in particular the multimetal oxide active compositions of the general stoichiometry II $$Mo_1V_bM^1_cM^2_dO_n \tag{II}$$

where the variables are as defined with regard to the stoichiometry I and n is a number which is determined by the valency and frequency of the elements in (II) other than oxygen.

The relevant multimetal oxide active compositions preferably contain the element combinations cited at the outset in the stoichiometry III $$Mo_1V_{a'}M^4_{b'}M^5_{c'}M^6_{d'} \tag{III}$$

where
$M^4$=at least one of the elements from the group consisting of Te and Sb;
$M^5$=at least one of the elements from the group consisting of Nb, Ti, W, Ta and Ce;
$M^6$=at least one of the elements from the group consisting of Pb, Ni, Co, Bi, Pd, Cs, Ca, Sr, Ba, Ag, Pt, Cu, Au, Ga, Zn, Sn, In, Re, Ir, Sm, Sc, Y, Pr, Nd and Tb;
a'=from 0.01 to 1;
b'=from >0 to 1;
c'=from >0 to 1; and
d'=from 0 to 0.5.

a' is preferably from 0.05 to 0.6, more preferably from 0.1 to 0.6 or 0.5.

b' is preferably from 0.01 to 1, more preferably from 0.01 or 0.1 to 0.5 or 0.4.

c' is preferably from 0.01 to 1, more preferably from 0.01 or 0.1 to 0.5 or 0.4.

d' is preferably from 0.00005 or 0.0005 to 0.5, more preferably from 0.001 to 0.5, frequently from 0.002 to 0.3 and often from 0.005 or 0.01 to 0.1.

$M^4$ is preferably Te.

$M^5$ is Nb, preferably in at least 50 mol % of its total amount, with preference at least 75 mol % and most preferably at least 100 mol %.

$M^6$ is preferably at least one element from the group consisting of Ni, Co, Bi, Pd, Ag, Au, Pb and Ga, more preferably at least one element from the group consisting of Ni, Co, Pd and Bi.

Very particular preference is given to at least 50 mol %, or at least 75 mol %, or 100 mol %, of the total amount of $M^5$ being Nb, and $M^6$ being at least one element from the group consisting of Ni, Co, Pd and Bi.

Outstanding in accordance with the invention is $M^4$=Te, $M^5$=Nb and $M^6$ is at least one element from the group consisting of Ni, Co and Pd.

The aforementioned is especially true when the active composition of the catalyst charge, with regard to its elements other than oxygen, consists of an element combination of the stoichiometry (III). These are then in particular the multimetal oxide active compositions of the general stoichiometry (IV)

where the variables are each as defined with regard to the stoichiometry III and n' is a number which is determined by the valency and frequency of the elements other than oxygen in (IV).

In the process according to the invention, preference is further given to using those multimetal oxide active compositions which, on the one hand, either contain one of the abovementioned element combinations (I) and (III) or, with regard to the elements other than oxygen, consist of them and, at the same time, have an X-ray diffractogram which exhibits reflections h and i whose peak locations are at the reflection angles (2θ) 22.2±0.5°(h) and 27.3±0.5° (i) (all the information relating to an X-ray diffractogram in this document relates to an X-ray diffractogram obtained using Cu-Kα radiation as the X-ray radiation (Siemens Theta-Theta D-5000 diffractometer, tube voltage: 40 kV, tube current: 40 mA, aperture V20 (variable), collimator V20 (variable), secondary monochromator aperture (0.1 mm), detector aperture (0.6 mm), measuring interval (2θ) 0.020, measurement time per step: 2.4 s, detector: scintillation counting tube).

The half-height width of these reflections may be very small or else very marked.

Favorable for the process according to the invention are those of the above-mentioned multimetal oxide active compositions whose X-ray diffractogram, in addition to the reflections h and i, has a reflection k whose peak location is at 28.2±0.5° (k).

Among the latter, preference is given according to the invention in turn to those in which the reflection h has the highest intensity within the X-ray diffractogram, and also a maximum half-height width of at most 0.50, and very particular preference is given to those in which the half-height width of the reflection i and of the reflection k are at the same time ≦10 and the intensity $P_k$ of the reflection k and the intensity $P_i$ of the reflection i fulfill the relationship 0.2≦R≦0.85, better 0.3≦R≦0.85, preferably 0.4≦R≦0.85, particularly preferably 0.65≦R≦0.85, even more preferably 0.67≦R≦0.75 and very particularly preferably R=from 0.70 to 0.75 or R 0.72 where R is the intensity ratio defined by the formula $$R=P_i/(P_i+P_k)$$

Preferably, the abovementioned X-ray diffractograms have no reflection whose maximum is at 2θ=50±0.3°.

The definition of the intensity of a reflection in the X-ray diffractogram in this document refers to the definition laid down in DE-A 19835247, DE-A 10122027, and also in DE-A 10051419 and DE-A 10046672. The same applies to the definition of the half-height width.

In addition to the reflections h, i and k, the abovementioned X-ray diffractograms of multimetal oxide active compositions to be used advantageously according to the invention contain still further reflections whose peak locations are at the following reflection angles (2θ):
9.0±0.40 (l)
6.7±0.4° (o) and
7.9±0.4° (p).

It is further advantageous when the X-ray diffractogram additionally contains a reflection whose peak location is at a reflection angle (2θ)=45.2±0.40° (q).

Frequently, the X-ray diffractogram also contains the reflections 29.2±0.4° (m) and 35.4±0.4° (n).

It is further advantageous when the element combinations defined in the formulae (I), (II), (III) and (IV) are present as a pure i-phase. When the catalytically active oxide composition also contains k-phase, its X-ray diffractogram contains, in addition to the abovementioned reflections, further reflections whose peak locations are at the following reflection angles (2θ): 36.2±0.4° and 50±0.40 (the terms i- and k-phase are used in this document as defined in DE-A 10122027 and DE-A 10119933).

When the intensity 100 is assigned to the reflection h, it is advantageous according to the invention when the reflections i, l, m, n, o, p and q, on the same intensity scale, have the following intensities:
i: from 5 to 95, frequently from 5 to 80, in some cases from 10 to 60;
l: from 1 to 30;
m: from 1 to 40;
n: from 1 to 40;
o: from 1 to 30;
p: from 1 to 30 and
q: from 5 to 60.

When the X-ray diffractogram contains the abovementioned additional reflections, the half-height width is generally ≦1°.

The specific surface area of multimetal oxide active compositions of the general formula (II) or (IV) to be used according to the invention or of multimetal oxide active compositions which contain element combinations of the general formula (I) or (III) is in many cases from 1 to 40 m²/g or 10 to 30 m²/g (BET surface area, nitrogen), in particular when their X-ray diffractogram is as described.

The preparation of the multimetal oxide active compositions described can be found in connection with this cited prior art. This includes in particular DE-A 10303526, DE-A 10261186, DE-A 10254279, DE-A 10254278, DE-A 10122027, DE-A 10119933, DE-A 10033121, EP-A 1192987, DE-A 10029338, JP-A 2000-143244, EP-A 962253, EP-A 895809, DE-A 19835247, WO 00/29105, WO 00/29106, EP-A 529853 and EP-A 608838 (in all implementation examples of the last two documents, the drying method to be applied is spray drying; for example, at an inlet temperature of from 300 to 350° C. and an outlet temperature of from 100 to 150° C.; cocurrent or countercurrent).

The multimetal oxide active compositions described may be used as such (i.e. in powder form) or shaped to suitable geometries (cf., for example, the coated catalysts of DE-A 10051419 and also the geometric variants of DE-A 10122027) for the process according to the invention. They are outstandingly suitable for preparing acrylic acid from propane, but also for preparing methacrylic acid from isobutane.

To carry out the process according to the invention, all catalysts mentioned can be used either undiluted or diluted with inert particles and/or shaped bodies (they have no active composition). A suitable diluent material is, for example, steatite.

The geometry of the shaped diluent bodies is preferably identical to that of the shaped catalyst bodies.

As described in the documents on multimetal oxide active composition catalysts suitable for the process according to the invention, the process according to the invention can be carried out either over fixed bed catalyst charges or over fluidized bed catalyst charges. The reaction stage inlet pressures which can be employed in accordance with the invention have already been described.

The reaction temperatures, especially when employing the catalysts recommended in this document, may be from 200 to 700° C., preferably from 200 to 550° C. or from 230 to 480° C. or from 300 to 440° C.

The hourly space velocity of the propane and/or isobutane on the catalyst charge may be from 50 to 3000 l(STP)/l (catalyst charge)/h, or from 80 to 1500 l(STP)/l/h, or from 100 to 1000 l(STP)/l/h, or from 120 to 600 l(STP)/l/h, or from 140 to 300 l(STP)/l/h.

The hourly space velocity of starting reaction gas mixture on the catalyst charge may be from 100 to 10 000 l(STP)/l/h, or from 300 to 6000 l(STP)/l/h, or from 300 to 2000 l(STP)/l/h. The average residence time in the catalyst charge may be from 0.01 to 10 s, or from 0.1 to 10 s, or from 2 to 6 s.

In the case of a preparation of acrylic acid from propane, or of methacrylic acid from isobutane, the starting reaction gas mixture may contain, for example:
from 0.5 to 15, frequently from 1 to 7, % by volume of propane or isobutane
from 10 to 90, frequently from 20 to 50, % by volume of air,
from 0 to 50% by volume of steam and
a remainder of cycle gas.

However, in the case of a preparation of acrylic acid from propane, or of methacrylic acid from isobutene for the process of the invention, the starting reaction gas mixture may also contain:
from 0.6 to 1.2% by volume of propane or isobutene,
from 65 to 95% by volume of air,
from 2 to 30% by volume of nitrogen,
from 0.05 to 0.8% by volume of $CO_x$ and
from 2 to 3% by volume of steam.

Preference is given to starting reaction gas mixtures which contain from 10 to 50% by volume of steam (fresh).

Another possible composition of the starting reaction gas mixture may contain, for example,
from 70 to 90% by volume of propane or isobutene,
from 5 to 25% by volume of molecular oxygen,
from 0 to 25% by volume of steam and
a remainder of cycle gas.

Preference is also given here to starting reaction gas mixtures which contain a total of from 10 to 50% by volume of steam. In other words, the composition of the starting reaction gas mixture for the process according to the invention in the case of a propane or isobutane partial oxidation typically varies within the following range (molar ratios):

isobutane or propane:oxygen:$H_2O$:other diluent gases =
1:(0.1-10):(0-50):(0-50), preferably
1:(0.1-10):(0.1-50):(1-50), more preferably
1:(0.5-5):(1-30):(1-30).

The aforementioned ranges apply in particular when the other diluent gases used are predominantly molecular nitrogen. Other possible diluent gases are, for example, He, Ar, CO and/or $CO_2$ etc.

Quite generally, the composition of the starting reaction gas mixture is selected in such as way that it is preferably outside the explosion gas range.

When the process according to the invention is carried out as a partial oxidation, this may be effected, for example, in one-zone tube bundle reactors, as described in EP-A 700714 and in EP-A 700893. However, it can also be performed in multizone tube bundle reactors, as described in DE-A 19927624, DE-A 19948242, DE-A 19948241, DE-A 19910508 and DE-A 19910506. The process according to the invention can be carried out in a fluidized bed, for example as described in WO 02/0811421.

Based on the propane and/or isobutane present in the starting reaction gas mixture, the conversion of propane and/or isobutane in the process according to the invention, based on single pass of the reaction gas mixture through the reaction stage, will generally be from 10 or 20 to 70 mol %, frequently from 30 to 60 mol % and in many cases from 40 to 60 mol % or from 45 to 55 mol %. The selectivity of target product formation will typically be from 40 to 98 or 95 or to 90 mol %, frequently from 50 to 80 mol %, often from 60 to 80 mol %.

The basic separation of the at least one target product from product gas mixture resulting in the reaction stage of the process according to the invention can in principle be carried out in the inventive workup stage in such a manner as known from the prior art processes. In particular, in accordance with the invention, the workup processes can also be employed which are disclosed in the prior art for the basic separation of the same target products from product gas mixtures, as known in the preparation of the target products by heterogeneously catalyzed partial oxidation of propene and/or isobutene.

In general, the product gas mixture which results in the reaction stage in the process according to the invention, on entry into the inventive workup stage, will initially be subjected to indirect and/or direct cooling.

For the purpose of the basic separation of target product present in the product gas mixture into a liquid phase, the product gas mixture which has been cooled in this way (in the case of acrylic acid, for example, typically to 150-250° C.) or else uncooled product gas mixture can be conducted, for example, in an absorption column in countercurrent to descending liquid absorbent which absorbs the at least one target product substantially selectively from the product gas mixture, as described, for example, by JP-A 2001/0026269, EP-A 990636, JP-A 2000/327651, EP-A 925272, EP-A 695736, EP-A 778255, DE-A 2136396, DE-A 2449780, DE-A 4308087, EP-A 982287, EP-A 982289, EP-A 982288 and DE-A 19631645 for the target products and different absorbents.

Useful absorbents for substantially both target products are either water (or aqueous mixtures, for example aqueous sodium hydroxide solution or aqueous acrylic acid or methacrylic acid), alcohols used for esterifying acrylic acid and methacrylic acid, e.g. 2-ethylhexanol, or else relatively high-boiling organic solvents. Preference is given in accordance with the invention to the boiling point of the organic solvent being at least 20° C., in particular at least 50° C. and more preferably at least 70° C., above the boiling point of the target product to be removed from the product gas mixture (acrylic acid and/or methacrylic acid). Organic absorbents which are preferred in accordance with the invention have boiling points (at atmospheric pressure) of from 180 to 400° C., in particular from 220 to 360° C. In the case of the target products acrylic acid and methacrylic acid, particularly suitable absorbents in accordance with the invention are high-boiling, extremely hydrophobic solvents which contain no externally acting polar groups, such as aliphatic or aromatic hydrocarbons, for example middle oil fractions from paraffin distillation, or ethers having bulky groups on the oxygen atom, or mixtures thereof, to which it is advantageous to add a polar solvent, like the 1,2-dimethyl phthalate disclosed in DE-A 4308087. Also suitable are esters of benzoic acid and phthalic acid with straight-chain alkanols which contain from 1 to 8 carbon atoms, such as n-butyl benzoate, methyl benzoate, ethyl benzoate, dimethyl phthalate, diethyl phthalate, and also what are known as heat carrier oils, such as diphenyl, diphenyl ether and mixtures of diphenyl and diphenyl ether, or their chlorine derivatives and triarylalkanes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers.

A particularly preferred absorbent for acrylic acid (methacrylic acid is preferably absorbed into water) is a solvent mixture of diphenyl- and diphenyl ether, preferably in the azeotropic composition, in particular of about 25% by weight of diphenyl (biphenyl) and about 75% by weight of diphenyl ether, based on 100% by weight of diphenyl and diphenyl ether, for example the Diphyl® obtainable commercially. This solvent mixture preferably also comprises a polar solvent such as dimethyl phthalate in an amount of from 0.1 to 25% by weight, based on the entire solvent mixture. Advantageously, when a high-boiling organic solvent is used as an absorbent, the product gas mixture is advantageously cooled before the absorption by partial evaporation of the absorbent in a direct condensor or quench apparatus. Suitable for this purpose are in particular Venturi scrubbers, bubble columns or spray condensors.

In this document, the terms high boilers, middle boilers and low boilers mean compounds which have a higher boiling point than the target compound (high boilers), about the same boiling point as the target compound (middle boilers) and a lower boiling point than the target compound (low boilers) respectively, especially when the target compound is acrylic acid.

Quite generally, the countercurrent absorption is preferably effected in a column having structured packings or random packings or in a tray column which is preferably equipped with dual-flow trays and/or valve trays and which is charged from above with solvent the product gas mixture (and optionally evaporated absorbent from the quench apparatus) is passed into the column from below and subsequently cooled to absorption temperature. The cooling is advantageously effected by cooling circuits. In other words, heated absorbent rising in the column is removed from the column, cooled in heat exchangers and recycled back into the absorption column at a point above the takeoff point. After the absorption, substantially all high boilers, the majority of the target compound (for example acrylic acid) and a portion of the low boilers are in the absorbent. The manner in which the target product can then be further removed in any desired purity (for example as in DE-A 19606877 or in DE-A 19838845) from the absorbate containing the target compound (for example acrylic acid) which has been basically separated may be as described in the prior art (for example that cited for the absorption), and absorbent which has been freed of target product can be reused in the absorption (for example, by removing the acrylic acid overhead from the organic absorbent in the organic absorbate and further purifying rectificatively and/or crystallizatively (for example suspension crystallization with crystal removal in a melt washing column) or further removing the water from the aqueous absorbate rectificatively overhead by means of an organic azeotroping agent and the acrylic acid from the acrylic acid-containing liquid phase rectificatively and/or crystallizatively in any desired purity; in the latter case, the top product is generally separated into two phases (by cooling); the organic phase is recycled into the rectification column and the aqueous phase into the absorption column (in each case at the top of the column)).

The remaining, unabsorbed residual product gas mixture can be further cooled in order to remove the easily condensible portion of the low-boiling secondary components (for example water, formaldehyde and acetic acid) (generally referred to as acid water). According to the invention, the remaining residual product gas mixture can be divided into two portions and one of the two portions can be recycled as cycle gas (into the reaction stage) and the other portion discharged. According to the invention, there is preferably no acid water removal. Especially when steam is used as diluent gas in the reaction stage of the process according to the invention (when multimetal oxide compositions (I), (II), (III) or (IV) are used this is generally advantageous for the selectivity of the target product formation), the inventive basic separation of target product present in the product gas mixture of the reaction stage into the liquid phase (irrespective of which separating process is employed, in particular of those described in this document) is preferably effected in such a way that the remaining residual product gas mixture of which at least a portion is to be recycled (as cycle gas) in accordance with the invention into the reaction stage, the molar ratio W of the steam present therein to the propane present therein is at most 50%, better at most 40 or 30%, even better at most 20 or 10%, preferably at most 5%, smaller than the corresponding molar ratio W' in the product gas mixture of the reaction stage. In the extreme case, the aforementioned ratios W and W' in the process according to the invention may also be identical.

The attempt to leave as much steam as possible in the residual product gas mixture here has the purpose of being able to very substantially dispense with a fresh feed (or condensation and re-evaporation) of steam into the starting reaction gas mixture.

However, the portion of the residual product gas mixture which is discharged as output in the process according to the invention has to contain at least as much water as is by-produced in the reaction stage, in order to prevent accumulation of the water in the reaction gas mixture (the more selectively the reaction is conducted in the reaction stage, the smaller the amount of water to be discharged). This also applies correspondingly to other secondary components formed in the reaction stage. When air is used in the process according to the invention as the oxygen source, the output amount of residual product gas mixture at the same time has to be such that the amount of nitrogen present therein at least corresponds to that which is present in the air feed.

When the absorbent used is one of the high-boiling organic solvents, the absorption in the present case will preferably be carried out in such a way (especially in the case of an absorption of acrylic acid) that the effluent from the absorption column is monophasic. Otherwise, the steam content in the residual product gas mixture remaining in the absorption, irrespective of the absorbent selected can be adjusted by suitable choice of the absorption temperature.

As an alternative to a basic separation of target product into a liquid phase by absorption into a solvent, this basic separation (especially in the case of acrylic acid) can also be effected by condensation, in particular fractional condensation, as described, for example, by DE-A 19924532, DE-A 10200583, DE-A 10053086, DE-A 19627847, DE-A 19740253, DE-A 19740252, DE-A 19740253, DE-A 19814387 and DE-A 10247240.

In this condensation, the product gas mixture of the reaction stage, optionally after direct and/or indirect precooling, is subjected in a separating column equipped with separating internals, ascending into itself, to a fractional condensation and the target product is removed via a sidestream of the separating column and subjected, as described in the prior art, to further crystallizative and/or rectificative separating steps.

Preferred condensation columns containing separating internals are tray columns whose separating internals from bottom to top are initially dual-flow trays and then hydraulically sealed crossflow trays, as described in the aforementioned prior art.

Preference is also given in accordance with the invention to carrying out the aforementioned fractional condensation in such a way that there is substantially no removal of water present in the product gas mixture. In other words, there is also no acid water removal here.

However, the portion of the residual product gas mixture discharged as output can still be washed with water before its output, in order to prevent methacrylic acid or acrylic acid losses. The acrylic acid or methacrylic acid and any other organic products of value can be extracted from the resulting methacrylic acid- or acrylic acid-containing acid water, for example using the organic absorbent used for absorption, and combined with the absorbate.

For the purpose of preventing increased pressure drops, both the absorption column and the column for fractional condensation may in principle also be replaced by a series connection of quench stages which are operated with absorbent or condensate.

Quite generally, the polymerization inhibition is effected in the course of the basic separation of target product from the product gas mixture into a liquid phase as described in the prior art of the appropriate polymerization inhibitors.

It is essential to the invention that the residual product gas mixture which remains in the basic separation of target product contains not only propane and/or isobutane and also in some cases propene and/or isobutene but also normally at least 5% by volume, usually at least 10% by volume, of constituents which have a lower boiling point than the target product at atmospheric pressure. These are in particular the constituents (for example $N_2$, $CO$, $CO_2$) of the product gas mixture which have a lower boiling point than water at atmospheric pressure, and also preferably water itself.

One advantage of the process according to the invention is that the cycle gas can generally be recompressed (from approx. outlet pressure $P^3$) to the inlet pressure $P^1$ by means of a blower. In this context, a blower is a compressor (normally an axial compressor) having a low pressure ratio (end pressure to outlet pressure such as 1.1:1 to 3:1). In contrast, air used as an oxygen source is normally compressed (from approx. ambient pressure) to the inlet pressure $P^1$ by means of a radial compressor. In principle, the compressions referred to in this document can be carried out isothermally or polytropically. Preference is given in accordance with the invention to the latter.

Some of the advantageousness of the inventive procedure is still retained even when the propane and/or isobutane and also any propene and/or isobutene present in the portion of the residual product gas mixture to be discharged, optionally after preceding condensative removal of the water fraction present therein (can be recycled into the reaction stage), are removed therefrom and recycled into the reaction stage recompressed to the inlet pressure $P^1$.

This removal (which is recommended in the prior art for the entire amount of the residual product gas mixture and can in principle also be employed (in particular as described hereinbelow)) will be carried out, for example, in such a way (cf. WO 0196271) that the propane and/or isobutane and also any propene and/or isobutene present in the portion of the residual product gas mixture to be discharged are removed absorptively and/or adsorptively and subsequently released again by desorbtion and/or desorption. For example, this release from the absorbate can be carried out by stripping with air, as described, for example, in WO 0196271. The air can subsequently also be compressed and also be recycled into the reaction stage.

Alternatively, the portion of the residual product gas mixture to be discharged can also be fed to a further oxidation reactor, optionally after supplementation of oxygen, in order to increase the carbon dioxide conversion.

In general, as already stated, a blower is sufficient for the purpose of recompressing the cycle gas in the process according to the invention.

The FIG. 1 accompanying this document shows an exemplary embodiment of the process according to the invention.

In this figure, the different numbers are defined as follows:
1=reaction stage
2=workup stage
3=cycle gas compressor (blower)
4=output expander
5=output
6=air as oxygen source
7=air compressor
8=fresh propane and/or isobutane and also optionally steam
9=recompressed cycle gas

EXAMPLES

1. Preparation of a Catalyst Having the Multimetal Oxide Active Composition $Mo_1V_{0.29}Te_{0.13}Nb_{0.13}O_x$ (Pure I-Phase)

87.61 g of ammonium metavanadate (78.55% by weight of V205, from G.f.E., Nuremberg) were dissolved at 80° C. in 3040 ml of water (three-neck flask equipped with stirrer, thermometer and reflux condensor). A clear yellowish solution was formed. This solution was cooled to 60° C. and then, while maintaining the 60° C., 117.03 g of telluric acid (99% by weight of $H_6TeO_6$, from Aldrich) and 400.00 g of ammonium heptamolybdate (82.52% by weight of $MoO_3$, from Starck, Goslar) were stirred in in succession. The resulting deep red solution was cooled to 30° C. (solution A).

In a beaker, 112.67 g of ammonium niobium oxalate (20.8% by weight of Nb, from Starck, Goslar) were dissolved separately at 60° C. in 500 ml of water (solution B).

Solution B was cooled to 30° C. and combined at this temperature with solution A by adding solution B to solution A. It was effected continuously over a period of approx. 5 minutes. An orange aqueous suspension with suspended precipitate was formed. This suspension was subsequently spray-dried ($T_{reservoir}$=30° C., $T^{in}$=320° C., $T^{out}$=110° C., t=1.5 h, spray tower from Niro of the atomizer type). The resulting sprayed material was likewise orange and contained the empirical stoichiometry $Mo_1V_{0.33}Te_{0.22}Nb_{0.11}$.

2×100 g of the spray powder were thermally treated in a rotary sphere oven according to FIG. 1 of DE-A 10119933 (1 l internal volume) by initially heating from 25° C. to 275° C. over 27.5 min with a linear heating ramp under an air stream of 50 l(STP)/h and subsequently holding this temperature for 1 h. Afterwards, the oven was heated from 275° C. to 600° C. with a linear heating ramp within 32.5 min, in the course of which the air stream was replaced by a 50 l(STP)/h nitrogen stream. While maintaining the nitrogen stream, the 600° C. were held for 2 h and the entire oven was subsequently allowed to cool to room temperature. 100 g of the resulting oxidic composition was stirred in 1000 ml of a 10% by weight aqueous $HNO_3$ solution at 70° C. under reflux for 7 h, and the remaining solid was filtered out of the resulting slurry and washed by means of water (25° C.) to free it of nitrate. The resulting filter cake was dried in a muffle furnace at 110° C. under air overnight. The chemical analysis of the resulting solid gave the composition $Mo_1V_{0.29}Te_{0.13}Nb_{0.13}O_x$. The accompanying X-ray diffractogram revealed pure i-phase.

Subsequently, the dried material, as described in DE-A 10119933, was ground in a Retsch mill (grain size≦0.12 mm) and, as in Example A) a) of DE-A 10119933, processed to give a coated catalyst:

38 g of ground active composition; 150 g of spherical support body having a diameter of from 2.2 to 3.2 mm (support material=Steatite C-220 from CeramTec, DE having a surface roughness Rz of 45 μm), tackifier=30 ml of a mixture of glycerol and water (glycerol:water weight ratio=1:3), drying time=16 h at 150° C.; the active composition fraction of the resulting coated catalyst was 20% by weight (based on the weight of the coated catalyst).

2. Heterogeneously Catalyzed Partial Direct Oxidation of Propane to Acrylic Acid at Different Pressures The coated catalyst from 1. was used to charge a reaction tube (length 140 cm) made of V2A steel (external diameter=60 mm, internal diameter=8.5 mm). The charge length selected was 53 cm (=approx. 35.0 g of the coated catalyst). A preliminary bed of length 30 cm of the steatite spheres used as support material served to position the catalyst zone. The same steatite spheres were used to finally fill the reaction tube after the catalyst zone (preheating zone for heating the starting reaction gas mixture). The reaction tube was heated from outside on its entire length by means of electrical heating mats. The molar composition of the starting reaction gas mixture was propane:air:water=1:15:14. The table which follows shows the resulting propane conversion on a single pass ($C^{PAN}$, mol %) and also the selectivity of acrylic acid formation ($S^{ACA}$, mol %) accompanying this conversion as a function of the selected inlet pressure and also the accompanying temperature of the heating mats. The residence time (based on the catalyst bed volume) was in all cases 2.4 s. In addition, the table indicates the selectivity of propene by-production by $S^{PEB}$.

TABLE

| Inlet pressure [bar, absolute] | T [° C.] | $C^{PAN}$ (mol %) | $S^{ACA}$ (mol %) | $S^{PEB}$ [mol %] |
|---|---|---|---|---|
| 1.3 | 390 | 28 | 70 | 10 |
| 1.3 | 440 | 53 | 39 | 5 |
| 6 | 330 | 32 | 69 | 5 |
| 6 | 350 | 50 | 70 | 3 |
| 6 | 390 | 77 | 60 | 1 |

At higher working pressure, higher propane conversions result at lower temperatures with substantially unchanged selectivity of the target product compound. Otherwise, the product gas mixture in all cases contains small amounts of further acids, for example acetic acid, and also COX.

Figure 2:
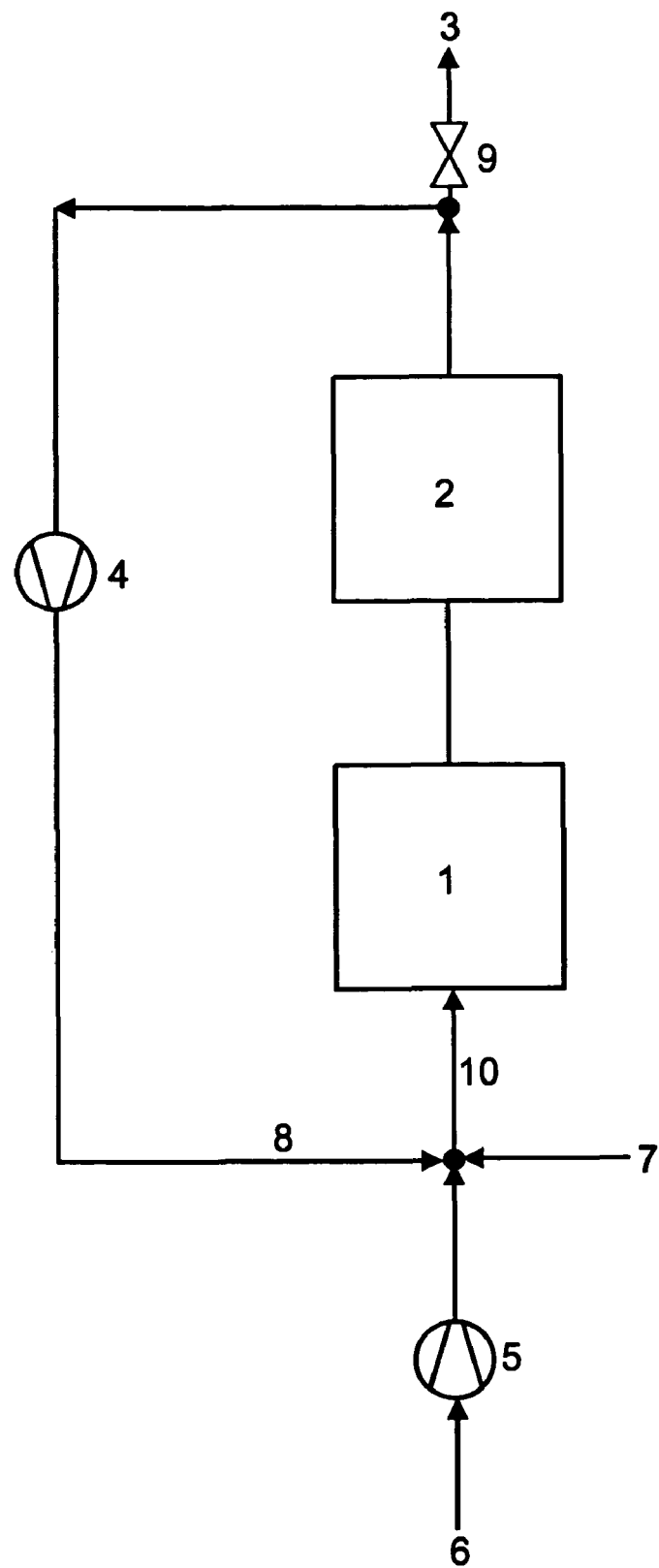

3. Isothermal Compressor Output Power in the Process According to the Invention as a Function of the Outlet Pressure $P^3$ at a Given Cycle Gas Ratio The process of 2. is carried out in an apparatus arrangement according to FIG. 2. The basis is a conversion of 40 mol % and a selectivity of acrylic acid formation of 70 mol %. The molar propane:oxygen:water composition corresponds to the composition in 2. The cycle gas control influences the nitrogen content. The different numbers are defined as follows:

1 reaction stage
2=workup stage
3=discharged portion of the residual product gas mixture
4=cycle gas compressor (blower)
5=air compressor
6=air as the oxygen source
7=fresh propane and fresh steam
8=recompressed cycle gas
9=throttle apparatus for regulating the outlet pressure $P^3$
10=starting reaction gas mixture with inlet pressure $P^1$.

The fresh propane and fresh steam are available at the inlet pressure required in each case.

In other words, a change in $P^3$ only effects the power of the cycle gas compressor and the power of the air compressor.

For the sake of simplicity, isothermal compression is assumed for both compressors.

According to VDI-Wärmeatlas, Verlag des Vereins Deutscher Ingenieure, Düsseldorf, 5$^{th}$ edition, 1988, sheet La 1, the isothermal compressor power of the air compressor ($V^L$) is:

$$V^L = \frac{\dot{m}_L}{n_L} \cdot Z_L \cdot R \cdot T_L \cdot \ln\left(\frac{P^1}{1}\right)$$

where
m*$_L$=fresh air flow rate;
$n_L$=efficiency of the air compressor;
$Z_L$=real gas factor for air;
R specific gas constant=ideal gas constant divided by the molar mass;
$T_L$=temperature at which the fresh air is aspirated from the environment;
1=atmospheric pressure (ambient pressure)=1 bar at which the air is aspirated;
$P^1$ inlet pressure into the reaction stage to which the air is compressed;
in other words, $V^L$=m*$_L$·A·ln·$P^1$, where A is a constant;
in a corresponding manner, the isothermal compressor power of the cycle gas compressor $V^K$ is:

$$V^K = \frac{\dot{m}_K}{n_K} \cdot Z_K \cdot R \cdot T_K \cdot \ln\frac{P^1}{P^3}.$$

In other words, $$V^K = \dot{m}_K \cdot A' \cdot \ln\frac{P^1}{P^3},$$

where A' is a constant for which: A'≈A.

Therefore, for the total compressor power $V_{ges}=V^L+V^K$ to be employed:

$$V_{ges} = \dot{m}_L \cdot A \cdot \ln \cdot P^1 + \dot{m}_K \cdot A' \ln\frac{P^1}{P^3}.$$

$$P^1 - P^3 = C \cdot \frac{1}{P^1},$$

where C is a constant which is characteristic for the reaction and workup apparatus used, and $$\frac{\dot{m}_K \cdot A'}{\dot{m}_L \cdot A} \approx \frac{\dot{m}_K}{\dot{m}_L} = K_r = \text{cycle gas ratio combined to give:}$$

$$V_{ges} = \dot{m}_K \cdot A \cdot \left[\left(1 + \frac{1}{K_r}\right)\ln\left(\frac{P^3}{2} + \sqrt{\left(\frac{P^3}{2}\right)^2 + C}\right) - \ln P^3\right].$$

Figure 3:
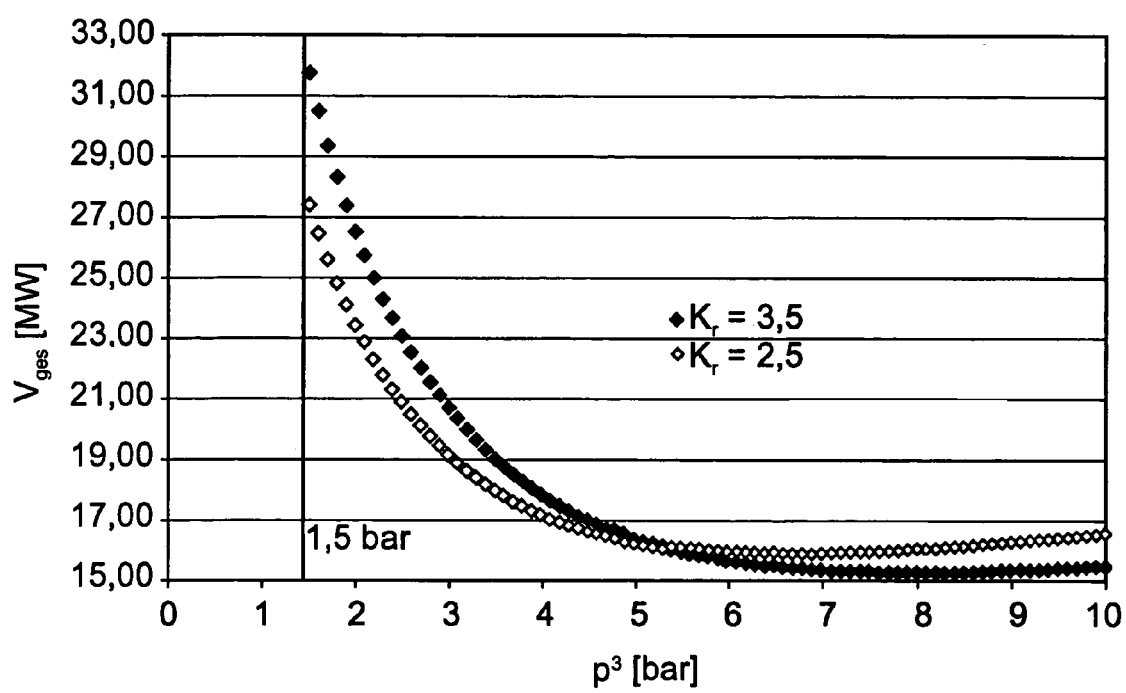

When the cycle gas ratio is selected once as 2.5 and once as 3.5, and the constant C is determined as $C=(1.5\ \text{bar}+\Delta P^{1.5})\cdot\Delta P_{1.5}$, where $\Delta P^{1.5}$ is the pressure drop suffered overall at an outlet pressure (outlet from workup stage) of 1.5 bar over the reaction stage and the workup stage, at a pressure drop which is representative for the process according to the invention of 2 bar, giving $C=(1.5\ \text{bar}+2\ \text{bar})\ 2\ \text{bar}=7\ \text{bar}^2$, this gives (the $\dot{m}^*_K$ values are selected in such a way that the space-time yield of acrylic acid is the same in both cases), at $K_r=2.5$ with the cycle gas flowrate $\dot{m}^*_K=166$ kg/sec and at $K_r=3.5$ with the cycle gas flowrate $\dot{m}^*_K=213$ kg/sec, for the two selected cycle gas ratios, the plots shown in FIG. 3 of $V_{ges}$ as a function of $P^3$ (under the assumption, which is conservative according to the results in 2., of constant conversion and selectivity with increasing pressure).

Starting from $P^3=1.5$ bar, the compressor power to be employed overall increases with increasing $P^3$ in both cases, which proves the advantageousness of the inventive procedure.

We claim:

1. A process for heterogeneously catalyzed partial direct oxidation of propane and/or isobutane to at least one of the target products acrylic acid, methacrylic acid, by feeding a starting reaction gas mixture comprising propane and/or isobutane, molecular oxygen and at least one inert diluent gas and having a inlet pressure $P^1$ to a reaction stage which, apart from an inlet for the starting reaction gas mixture, optionally further inlets for auxiliary gases, and an outlet for the product gas mixture, is sealed on the gas side, in the reaction stage directly oxidizing the propane and/or isobutane present in the starting reaction gas mixture partially to at least one target product by passing the starting reaction gas mixture at elevated temperature over a solid state catalyst, and conducting the reaction gas mixture as a product gas mixture comprising at least one target product and having the outlet pressure $P^2$ out of the reaction stage and, with this pressure $P^2$, into a workup stage which, apart from an inlet for the product gas mixture, optionally further inlets for auxiliary gases, and an outlet for the residual product gas mixture, is sealed on the gas side, in the workup stage basically separating target product present in the product gas mixture of the reaction stage from said product gas mixture into a liquid phase and conducting the remaining residual product gas mixture which comprises not only propane and/or isobutane and also in some cases propene and/or isobutene and has the outlet pressure $P^3$, where $P^3<P^1$, out of the workup stage and recycling propane and/or isobutane present in the residual product gas mixture into the reaction stage, which comprises selecting $P^1$ in such a way that $P^3 \geq 1.5$ bar and dividing the residual product gas mixture into two portions of the same composition and discharging one portion as output and recycling the other portion as cycle gas and feeding it back to the reaction stage, compressed to the inlet pressure $P^1$, as a constituent of the starting reaction gas mixture.

2. The process as claimed in claim 1, wherein the residual product gas mixture contains at least 5% by volume of constituents other than propane and/or isobutane and also other than propene and/or isobutene.

3. The process as claimed in claim 1, wherein the residual product gas mixture contains at least 10% by volume of constituents other than propane and/or isobutane and also other than propene and/or isobutene.

4. The process as claimed in claim 1, wherein the pressure $P^3 \geq 1.5$ bar and $\leq 25$ bar.

5. The process as claimed in claim 1, wherein the pressure $P^3 \geq 1.5$ bar and $\leq 20$ bar.

6. The process as claimed in claim 1, wherein the pressure $P^3 \geq 1.5$ bar and $\leq 10$ bar.

7. The process as claimed in claim 1, wherein the pressure $P^3 \geq 2$ bar and $\leq 8$ bar.

8. The process as claimed in claim 1, wherein the pressure $P^1$ is from 1 to 4 bar above the pressure $P^3$.

9. The process as claimed in claim 1, wherein the pressure $P^1$ is from 1.5 to 3.5 bar above the pressure $P^3$.

10. The process as claimed in claim 1, wherein $P^1$ is from 3 to 10 bar.

11. The process as claimed in claim 1, wherein $P^1$ is from 4 to 8 bar.

12. The process as claimed in claim 1, wherein the portion of the residual product gas mixture which is discharged as output is discharged via an expander.

13. The process as claimed in claim 1, wherein the reaction stage is a catalyst-charged tube bundle reactor or fluidized bed reactor.

14. The process as claimed in claim 1, wherein the workup stage is an absorption column or a column for fractional condensation or a series arrangement of quench stages.

15. The process as claimed in claim 1, wherein the active composition of the catalyst is a multimetal oxide composition which comprises the elements Mo, V, at least one of the two elements Te and Sb, and at least one of the elements from the group consisting of Nb, Ta, W, Ti, Al, Zr, Cr, Mn, Ga, Fe, Ru, Co, Cs, Ca, Sr, Ba, Rh, Ni, Pd, Pt, La, Pb, Cu, Re, Ir, Y, Pr, Nd, Tb, Bi, B, Ce, Sn, Zn, Si, Na, Li, K, Mg, Ag, Au and In in combination.

16. The process as claimed in claim 1, wherein the active composition of the catalyst is a multimetal oxide composition which contains the element combination having the stoichiometry I $$Mo_1V_bM^1_cM^2_d \quad (I),$$

where
M$^1$=Te and/or Sb,
M$^2$=at least one of the elements from the group consisting of Nb, Ta, W, Ti, Al, Zr, Cs, Ca, Sr, Ba, Cr, Mn, Ga, Fe, Ru, Co, Rh, Ni, Pd, Pt, La, Bi, Pb, Cu, Re, Ir, Y, Pr, Nd, Tb, Ce, Sn, Zn, Si, Na, Li, K, Mg, Ag, Au and In,
b=from 0.01 to 1
c=from >0 to 1 and
d=from >0 to 1.

17. The process as claimed in claim 1, wherein the oxygen source used is air.

18. The process as claimed in claim 1, wherein the reaction temperature is from 200 to 700° C.

19. The process as claimed in claim 1, wherein the starting reaction gas mixture contains
from 0.5 to 15% by volume of propane or isobutane,
from 10 to 90% by volume of air,
from 0 to 50% by volume of steam and
a remainder of cycle gas.

20. The process as claimed in claim 1, wherein the starting reaction gas mixture contains
from 0.5 to 15% by volume of propane or isobutane,
from 10 to 90% by volume of air,
from 10 to 50% by volume of steam and
a remainder of cycle gas.

21. The process as claimed in claim 1, wherein the starting reaction gas mixture contains
from 70 to 90% by volume of propane or isobutane,
from 5 to 25% by volume of molecular oxygen,
from 0 to 25% by volume of steam and
a remainder of cycle gas.

22. The process as claimed in claim 1, wherein the conversion from propane and/or isobutane, based on single pass of the reaction gas mixture through the reaction stage, is from 10 to 70 mol %.

23. The process as claimed in claim 22, wherein the selectivity of the target product formation is from 40 to 98 mol %.

24. The process as claimed in claim 1, wherein the target product present in the product gas mixture of the reaction stage is basically separated into the liquid phase in such a way that the molar ratio W of the steam present in the remaining residual product gas mixture to the propane present therein is at least 50% smaller than the corresponding molar ratio W' in the product gas mixture of the reaction stage.

25. The process as claimed in claim 1, wherein the target product present in the product gas mixture of the reaction stage is basically separated into the liquid phase in an absorption column by absorption into an organic solvent in such a way that the discharge from the absorption column is monophasic.

26. The process as claimed in claim 1, wherein the propane and/or isobutane and also any propene and/or isobutene present in the portion of the residual product gas mixture which is discharged as output are removed from said residual product gas mixture and recycled into the reaction stage, recompressed to the inlet pressure P$^1$.

27. The process as claimed in claim 1, wherein the ratio V of that portion of the residual product gas mixture which is recycled as cycle gas to that portion of the residual product gas mixture which is discharged as output is ≧0.5 and ≦30.

28. The process as claimed in claim 1, wherein the ratio V of that portion of the residual product gas mixture which is recycled as cycle gas to that portion of the residual product gas mixture which is discharged as output is ≧2 and ≦25.

29. The process as claimed in claim 1, wherein the ratio V of that portion of the residual product gas mixture which is recycled as cycle gas to that portion of the residual product gas mixture which is discharged as output is ≧3 and ≦20.

30. The process as claimed in claim 1, wherein the cycle gas is recompressed to the inlet pressure P$^1$ using a blower.

31. The process as claimed in claim 1, wherein the oxygen source used is air which is compressed to the inlet pressure P$^1$ by means of a radial compressor.

32. The process as claimed in claim 1, which is a process for partial direct oxidation of propane to acrylic acid.

* * * * *